(12) United States Patent
Pan et al.

(10) Patent No.: US 9,237,875 B2
(45) Date of Patent: Jan. 19, 2016

(54) COLLIMATOR AND CT SYSTEM COMPRISING THE SAME

(71) Applicant: GE Medical Systems Global Technology Company, LLC, Waukesha, WI (US)

(72) Inventors: Xianjun Pan, Beijing (CN); Zhiyong Fu, Beijing (CN); Shutao Liu, Chengdu (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 41 days.

(21) Appl. No.: 14/089,877

(22) Filed: Nov. 26, 2013

(65) Prior Publication Data

US 2014/0146949 A1 May 29, 2014

(30) Foreign Application Priority Data

Nov. 27, 2012 (CN) .......................... 2012 1 0489649

(51) Int. Cl.
| | |
|---|---|
| *G21K 1/04* | (2006.01) |
| *G21K 1/02* | (2006.01) |
| *G02B 27/30* | (2006.01) |
| *A61B 6/06* | (2006.01) |
| *A61B 6/03* | (2006.01) |

(52) U.S. Cl.
CPC . *A61B 6/06* (2013.01); *G02B 27/30* (2013.01); *G21K 1/02* (2013.01); *G21K 1/04* (2013.01); *A61B 6/035* (2013.01)

(58) Field of Classification Search
CPC ........... G21K 1/02; G21K 1/04; G21K 1/046; A61B 6/06; G02B 27/30; G02B 27/09; G02B 27/0938; G02B 27/0988
USPC ........... 378/147, 150, 152, 204, 210; 359/641
See application file for complete search history.

(56) References Cited

U.S. PATENT DOCUMENTS

| | | | |
|---|---|---|---|
| 5,299,250 | A | 3/1994 | Styrnol |
| 6,301,334 | B1 | 10/2001 | Tybinkowski |
| 6,396,902 | B2 | 5/2002 | Tybinkowski |
| 7,317,786 | B2 | 1/2008 | Distler |
| 7,852,990 | B2 | 12/2010 | Aulbach |

*Primary Examiner* — Anastasia Midkiff
(74) *Attorney, Agent, or Firm* — GE Global Patent Operation

(57) ABSTRACT

A CT collimator comprising: a first gate and a second gate arranged in parallel on a slide rail, the first gate being fixed to a support rack of the CT collimator via elastic members; an electromagnet system arranged on one of the first gate and the second gate; and a metal plate arranged on the other side of the one of the first gate and the second gate relative to the electromagnet system, one end of the metal plate being fixed on the other of the first gate and the second gate and the other end of the metal plate extending to below the electromagnet system, wherein the electromagnet system is configured to engage the first gate and the second gate via the metal plate when the electromagnet system is triggered.

20 Claims, 3 Drawing Sheets

COLLIMATOR AND CT SYSTEM COMPRISING THE SAME

TECHNICAL FIELD

Embodiments of the present application relate to the field of radiograph CT, and more particularly, to a collimator having a single-motor drive system and a radiograph CT system comprising the same.

BACKGROUND ART

At present, radiograph CT systems such as X-ray CT system are widely used in various medical institutions for three-dimensional imaging of the regions of interest of the subjects to assist the clinicians to achieve an accurate medical diagnosis of the subjects.

In a radiograph CT system, a radiation source generating cone-shaped radiation beams and a radiation detector arranged on the other side of a subject relative to the radiation source and detecting the radiation beams rotate around a rotation center between the radiation source and the radiation detector. Projection data generated by the radiation beams transmitting through the subject are collected; based on the collected projection data, an image of the region of interest of the subject is reconstructed; and then the reconstructed CT image is displayed on an image display device.

In a radiograph CT system, a collimator is generally provided between the radiation source and the subject to be detected. By adjusting a width of the aperture of the collimator, the width of the radiation beams in a direction parallel to the subject is controlled so as to control a thickness of the scan slice.

A conventional collimator generally has at least two different motor drive systems to meet the requirements of multi-slot opening and Z tracking. Such a collimator comprises at least two gates or cams, which are driven by at least two different motor drive systems, and hence have higher cost, despite the fact that excellent performance is ensured by using at least two motor drive systems.

Some newly developed collimators use a single-motor drive system to meet the requirements of opening and Z tracking. Typically, such type of collimator comprises a plate or a star-shaped rotor having a plurality of slots driven by a single-motor drive system. Each slot corresponds to a collimator aperture of a different width. Said type of collimator can only show apertures of a fixed number and width; and during its rotation, the star-shaped rotor for Z tracking will include a different amplitude coefficient, due to a difference in distance from the two beam guiding edges to the curved surface detector.

SUMMARY OF THE INVENTION

The present invention provides a collimator and a CT system comprising the collimator capable of solving the above problems.

According to an embodiment of the present invention, there is provided a CT collimator. In an embodiment, the CT collimator comprises a first gate and a second gate arranged in parallel on a slide rail, the first gate being fixed to a support rack of the CT collimator via elastic members; an electromagnet system arranged on one of the first gate and the second gate; and a metal plate arranged on the other side of the first gate and the second gate relative to the electromagnet system, one end of the metal plate being fixed on the other of the first gate and the second gate and the other end of the metal plate extending to below the electromagnet system, wherein the electromagnet system is configured to engage the first gate and the second gate via the metal plate when the electromagnet system is triggered.

An embodiment of the present invention further comprises a single-motor drive system for driving the second gate to move on the slide rail via an actuator.

In the CT collimator according to an embodiment of the present invention, the metal plate is a steel plate or non-metal magnetic material, and the metal plate has a length capable of extending to below the electromagnet system when a maximum aperture is formed between the first gate and the second gate.

In the CT collimator according to an embodiment of the present invention, the electromagnet system comprises an electromagnet and a support unit to support the electromagnet, the support unit fixing the electromagnet on the one of the first gate and the second gate and the electromagnet when triggered engaging the first gate and the second gate.

In the CT collimator according to an embodiment of the present invention, the electromagnet system comprises an electromagnet, a support unit to support the electromagnet, and an elastic member coupled to the electromagnet, wherein a metal plate is provided at an end of the electromagnet far away from the elastic member, the metal plate being housed in an opening provided on a support plate of the one of the first plate and the second plate; and the electromagnet when triggered engages the first gate and the second gate via the metal plate provided on the electromagnet and the metal plate fixed on the other of the first gate and the second gate.

In the CT collimator according to an embodiment of the present invention, the first gate comprises a support plate and a shielding material which is arranged proximate to one side of the second gate at the middle portion of the support plate; and the second gate comprises a support plate and a shielding material which is arranged proximate to one side of the first gate at the middle portion of the support plate, the shielding materials blocking radiation beams which enter the CT collimator via an opening on a housing of the CT collimator.

In the CT collimator according to an embodiment of the present invention, a width of the shielding material is arranged to gradually decrease from a center of the shielding material to two ends thereof along relative edges of the shielding material.

In the CT collimator according to an embodiment of the present invention, an aperture between the shielding materials has a rectangular shape, and the shielding materials have an arc structure whose center of circle is on a focal point of a radiation source outside the collimator.

In the CT collimator according to an embodiment of the present invention, the elastic member is a stretchable and/or compressible spring.

In the CT collimator according to an embodiment of the present invention, the spring is stretchable or compressible, and a length of the spring is arranged to enable a center of an aperture, formed between the shielding materials when the elastic member is not deformed, to deviate from the center of the opening so as to form a completely closed state.

In the CT collimator according to an embodiment of the present invention, the spring is stretchable and compressible, and a length of the spring is arranged to enable the center of the aperture, formed between the shielding materials when the elastic member is not deformed, to directly face the center of the opening.

According to an embodiment of the present invention, there is provided a radiograph CT system comprising a CT collimator according to an embodiment of the present invention.

In an radiograph CT system according to an embodiment of the present invention, the radiograph CT system is an X-ray CT system.

Using the CT collimator according to an embodiment of the present invention and using an electromagnet system to simplify the mechanical structure of the collimator are such that collimator aperture width adjustment, radiation beam tracking and Z tracking can be achieved only by using a single-motor drive system, thereby reaching a simple technical solution that the CT collimator costs less and has a continuously variable aperture width.

BRIEF DESCRIPTION OF THE DRAWINGS

In the following some exemplary embodiments of the present invention will be described in detail with reference to the accompanying drawings, in which like or similar elements are denoted by the same reference numerals, wherein.

DETAILED DESCRIPTION OF THE SPECIFIC EMBODIMENTS

In the following detailed description, exemplary embodiments of the present invention are described with reference to the accompanying drawings. However, it will be appreciated by persons skilled in the art that the present invention is not limited to these exemplary embodiments.

Figure 1A:
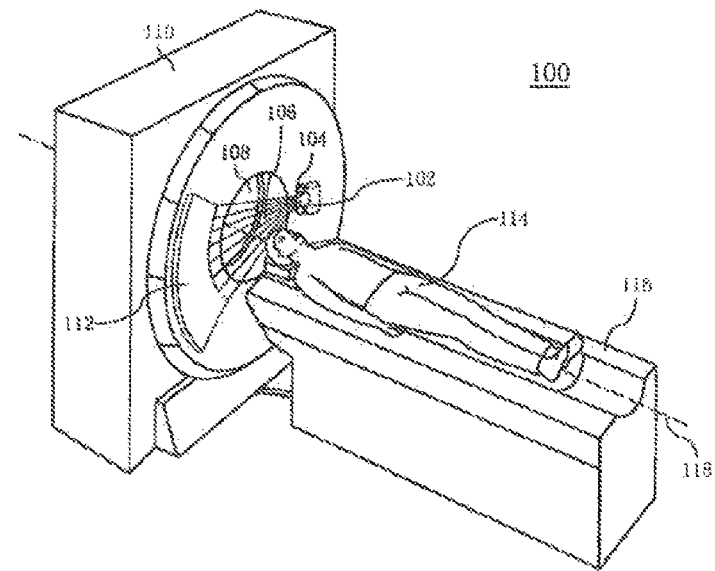
FIGS. 1A-1B show a radiograph CT system according to an exemplary embodiment of the present invention.
Figure 1B:
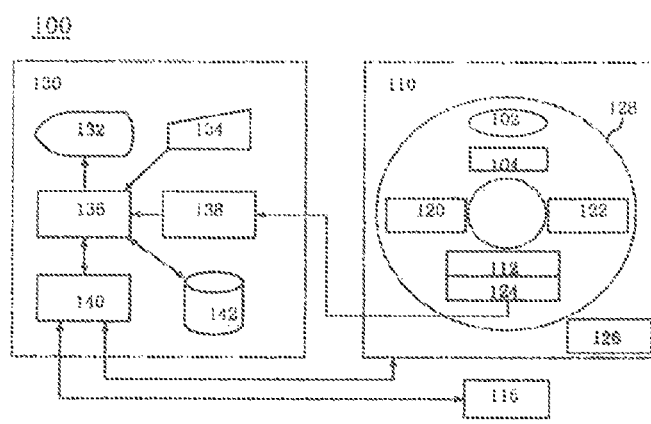

FIGS. 1A-1B show a radiograph CT system 100 according to an exemplary embodiment of the present invention. In an embodiment, the radiograph CT system 100 is an X-ray CT system.

As shown in FIGS. 1A-1B, the X-ray CT system 100 mainly includes three parts: a gantry 110, a scan table 116 for positioning a subject 114 to be detected, and an operation console 130. The gantry 110 includes an X-ray tube 102. X-rays 106 emitted from the X-ray tube 102 pass through a collimator 104 to form an X-ray beam of such shapes as fan shaped beam and cone shaped beam, to be irradiated to a region of interest of the subject 114. The X-ray beam that passes through the subject 114 is applied to an X-ray detector 112 disposed on the other side of the subject 114. The X-ray detector 112 has a plurality of two-dimensional X-ray detecting elements in the propagation direction (the channel direction) and the thickness direction (column direction) of the fan-shaped X-ray beam.

A data acquisition system (DAS) 124 is coupled to the X-ray detector 112. The data acquisition system 124 collects the data detected by each of the X-ray detecting elements of the X-ray detector 112 for use as the projection data. The X-ray radiation from the X-ray tube 102 is controlled by an X-ray controller 122. In FIG. 1B, the connections between the X-ray tube 102 and the X-ray controller 122 are not shown.

The data acquisition system 124 collects data related to the tube voltage and tube current applied to the X-ray tube 102 by the X-ray controller 122. In FIG. 1B, the connections between the X-ray controller 122 and the data acquisition system 124 are omitted.

The collimator 104 is controlled by a collimator controller 120. In an embodiment, the collimator 104 and the collimator controller 120 are two separate components. In another embodiment, the collimator controller 120 may be disposed within the collimator 104. In FIG. 1B, the connections between the collimator 104 and the collimator controller 120 are omitted.

Components like the X-ray tube 102, the collimator 104, the detector 112, the data acquisition system 124, the X-ray controller 122 and the collimator controller 120 are mounted in a rotating portion 128 of the gantry 110. The rotating portion 128 rotates under the control of a rotation controller 126. In FIG. 1B, the connections between the rotating portion 128 and the rotation controller 126 are not shown.

Under the action of a drive system such as a motor, the scan table 116 can be moved together with the subject 114 carried thereon along a longitudinal axis 118 of the subject into an opening 108 of the gantry 110, so that the region of interest of the subject 114 is substantially perpendicular to the X-ray beam irradiated thereon through the collimator 104.

The operation console 130 has a central processor 136 such as a computer. A control interface 140 is connected to the central processor 136. The gantry 110 and the scan table 116 are connected to the control interface 140. The central processor 136 controls the gantry 110 and the scan table 116 via the control interface 140.

The data acquisition system 124, the X-ray controller 122, the collimator controller 120 and the rotation controller 126 in the gantry 110 are controlled via the control interface 140. In FIG. 1B, the separate connections between the relevant parts and the control interface 140 are not shown.

A data acquisition buffer 138 is connected to the central processor 136. The data acquisition system 124 of the gantry 110 is connected to the data acquisition buffer 138. Projection data collected by the data acquisition system 124 are inputted to the central processor 136 via the data acquisition buffer 138.

The central processor 136 uses the projection data inputted from the data acquisition buffer 138 to perform an image reconstruction. In performing image reconstruction, such methods as the filtered back projection method, and three-dimensional image reconstruction method can be used. A storage device 142 is connected to the central processor 136. The storage device 142 may be used to store data, reconstructed images and procedures for implementing the various functions of the X-ray CT system 100.

A display device 132 and an input device 134 are connected to the central processor 136, respectively. The display device 132 displays the reconstructed images and other information output from the central processor 136. An operator can input various instructions and parameters to the central processor 136 via the input device 134. Through the display device 132 and the input device 134, the operator can achieve an interactive operation of the X-ray CT system 100.

FIGS. 2A-2D schematically show the structure of a radiograph CT collimator 104 according to an exemplary embodiment of the present invention. In an embodiment, the CT collimator 104 is an X-ray collimator.

Figure 2A:
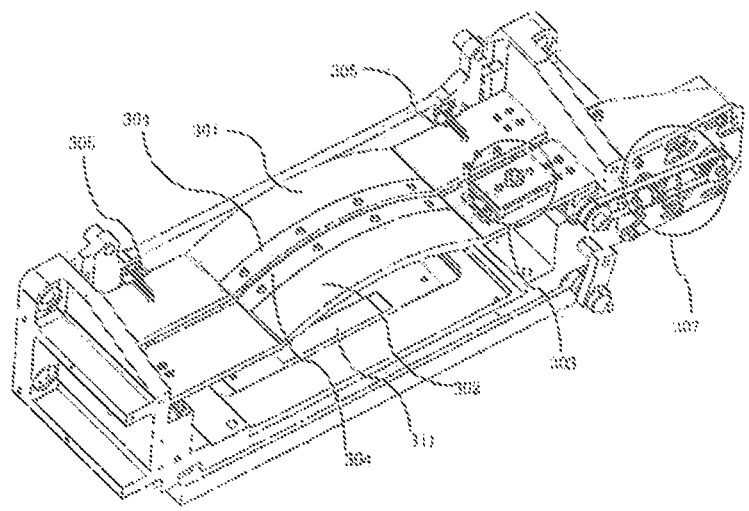
FIGS. 2A, 2B, 2C, and 2D show a CT collimator according to an exemplary embodiment of the present invention.

As shown in FIG. 2A, the CT collimator 104 mainly includes a secondary gate 301, a primary gate 302, an electromagnet system 303 and a metal plate 306 (which is not shown in FIG. 2A), elastic members 305, for example, spring, and a motor drive system 307. Therein, the metal plate 306 can be, for example, steel plate, or other non-metal magnetic material.

Figure 2B:
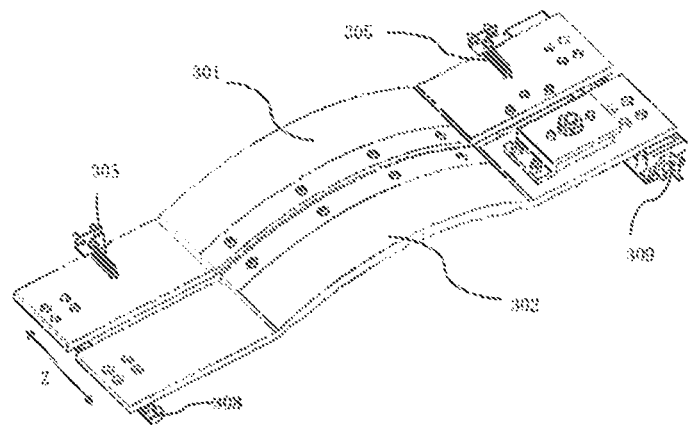
Figure 2C:
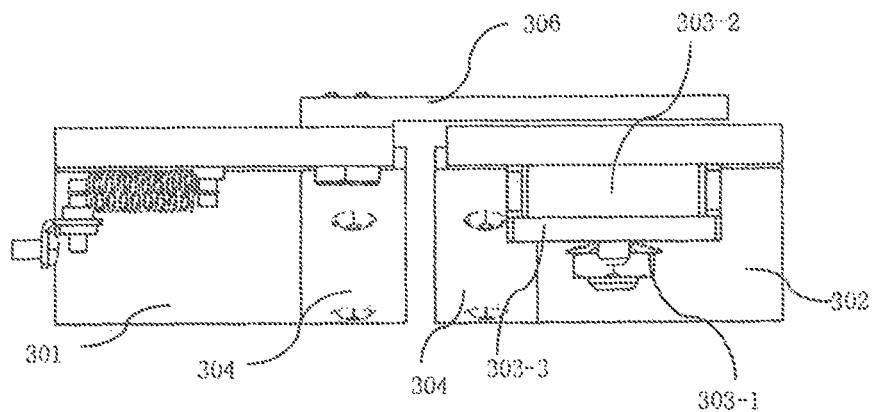
Figure 2D:
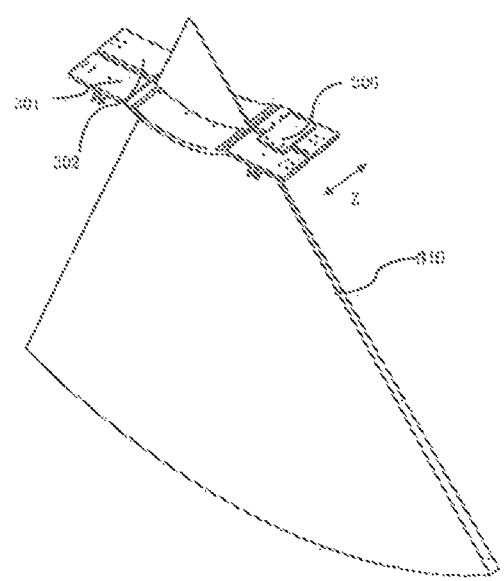

The secondary gate 301 is fixed to a support rack of the collimator 104 via the elastic members 305 disposed on both ends of the secondary gate 301. The primary gate 302 and the secondary gate 301 are arranged in parallel at a same horizontal plane. The primary gate 302 and the secondary gate 301 have both ends thereof arranged on the support rack of the collimator 104 via a slide rail 308. Under the action of the motor drive system 307 and the actuator 309, the primary gate 302 can move on the slide rail 38 along the Z-direction as shown in FIG. 2B or 2D.

An opening 311 is provided in a direction directly facing the X-ray tube 104 on a housing of the collimator 104. Through the opening 311 on the housing of the collimator 104, X-rays emitted from the X-ray tube 104 enter the collimator 104.

The primary gate 302 and the secondary gate 301 have a substantially identical structure. The primary gate 302 comprises a support plate and a shielding material 304 which is arranged proximate to one side of the secondary gate 301 at the middle portion of the support plate. Likewise, the secondary gate 301 comprises a support plate and a shielding material 304 which is arranged proximate to one side of the primary gate 302 at the middle portion of the support plate.

As required by the region of interest of a subject during CT scanning, the shielding materials 304 and the opening 311 are provided with appropriate dimensions. The shielding materials 304 provided on the primary gate 302 and the secondary gate 301 can block X-ray beams entering the collimator 104, so that the X-ray beams can only pass through the aperture between the two shielding materials 304 to be irradiated to the region of interest of the subject 114.

The elastic member 305 can be stretched and/or compressed along the Z direction as shown in FIG. 2B. Length and elasticity coefficient of the elastic member 305 are selected in a manner that the width of the aperture between the primary gate 302 and the secondary gate 301 satisfies the requirement for CT scanning when the secondary gate 301 moves along the Z direction on the slide rail 308. In an embodiment, the elastic member 305 can be stretched and compressed, and length of the elastic member 305 can be selected, such that when the elastic member 305 is not elastically deformed, the shielding materials provided on the primary gate 302 and the secondary gate 301 directly face the center of the opening 311 and are located downstream of the X-ray beams. In an embodiment, the elastic member 305 can be stretched or compressed, and length of the elastic member 305 can be selected, such that when the elastic member 305 is not elastically deformed, the shielding materials 304 provided on the primary gate 302 and the secondary gate 301 deviate from the center of the opening 311 and are located downstream of the X-ray beams so as to form a completely closed state.

In an embodiment, the middle portions of the primary gate 302 and the secondary gate 301 comprise the shielding materials 304 having a planar structure. Width of the shielding material 304 is arranged to gradually decrease from a center of the shielding material 304 to two ends thereof along relative edges of the shielding material 304, so that the opening formed between the two shielding materials 304 has a non-rectangular shape, thereby forming an X-ray detection area of a rectangular shape on the X-ray detector 112.

In an embodiment, the middle portions of the primary gate 302 and the secondary gate 301 comprise the shielding materials 304 having an arc structure, as shown in FIGS. 2A and 2B. The arc structure and the arc structure of the detector 112 which is disposed on the other side of the subject 114 each have a center of circle which is on a focal point of the X-ray tube 102, as shown in FIG. 2D.

As shown in FIG. 2A, the electromagnet system 303 is arranged on one end of the primary gate 302. The metal plate 306 is arranged the other side of the primary gate 302 relative to the electromagnet system 303, as shown in FIG. 2C or 2D. One end of the metal plate 306 is fixed on the secondary gate 301, and a space is formed between the end of the metal plate 306 and a surface of the primary gate 302; and the other end of the metal plate 306 extends to below the electromagnet system 303 provided on the primary gate 302.

Optionally, the electromagnet system 303 can be arranged on one end of the secondary gate 301. The metal plate 306 can be arranged on the other side of the secondary gate 301 relative to the electromagnet system 303. One end of the metal plate 306 is fixed on the primary gate 302, and a space is formed between the end of the metal plate 306 and the surface of the secondary gate 301; and the other end of the metal plate 306 extends to below the electromagnet system 303 provided on the secondary gate 301.

The metal plate 306 has a substantially planar structure, and its length is such that the metal plate 306 can still extend to below the electromagnet system 303 when a maximum aperture is formed between the primary gate 302 and the secondary gate 301.

In an embodiment, the electromagnet system 303 may include an electromagnet 303-2 and a support unit 303-3. The support unit 303-3 supports the electromagnet 303-2, and fixes it to a support plate of the primary gate 302 or the secondary gate 301, as shown in FIG. 2B. The electromagnet 303-2 can be a conventional electromagnet including an iron core and a coil winding around the iron core. Under the action of a power source (not shown), the electromagnet 303-2 of the electromagnet system 303 is triggered to generate an electromagnetic force, so as to closely engage the metal plate 306 fixed on the secondary gate 301 or the primary gate 302 and the support plate of the primary gate 302 or the secondary gate 301. Therefore, the primary gate 302 and the primary gate 301 can move together.

In an embodiment, the electromagnet system 303 may include an electromagnet 303-2, a support unit 303-3 to support the electromagnet 303-2, and an elastic member 303-1 coupled to the electromagnet 303-2 and fixed on the support unit 303-3, as shown in FIG. 2C. The electromagnet 303-2 can be a conventional electromagnet including an iron core and a coil winding around the iron core. The elastic member 303-1 can be a spring. A metal plate is provided at one end of the electromagnet 303-2 far away from the elastic member 303-1, and an opening is provided at the support plate of the primary gate 302 (being a secondary gate 301 when the electromagnet system 303 is disposed in the secondary gate 301 and the metal plate 306 is fixed to the primary gate 302) directly facing the metal plate, so as to house the metal plate disposed on one end of the electromagnet 303-2. The elastic member 303-1 is arranged in a manner that the metal plate on one end of the electromagnet 303-2 and the support plate of the primary gate 302 (being a secondary gate 301 when the electromagnet system 303 is disposed in the secondary gate 301 and the metal plate 306 is fixed to the primary gate 302) are at a substantially same plane when the electromagnet system 303 is not triggered. When the electromagnet 303-2 of the electromagnet system 303 is triggered by the power source, the metal plate on the electromagnet 303-2, under the action of the electromagnetic force, closely engages with the metal plate 306 fixed on the secondary gate 301 or the primary gate 302. Therefore, the primary gate 302 and the primary gate 301 can move together.

The electromagnet 303-2 and/or triggering power source can be selected according to such factors as elasticity of the elastic member 305 and the frictional force in engagement of the metal plate 306.

When a CT scan is performed on the subject 114, the operator selects a width of the aperture of the collimator 104 via the input device 134; the central processor 136 generates and transmits respective instructions to the collimator controller 120, which collimator controller 120 controls movement of the primary gate 302 via the motor drive system 307 so that width of the aperture between the primary gate 302 and the secondary gate 301 can meet the requirement. After the desired aperture width is obtained, the electromagnet system 303 is triggered, such that the primary gate 302 (being a secondary gate 301 when the electromagnet system 303 is disposed in the secondary gate 301 and the metal plate 306 is fixed to the primary gate 302) or the electromagnet system 303 closely engages with the metal plate 306 fixed to the secondary gate 301 (being a primary gate 302 when the electromagnet system 303 is disposed in the secondary gate 301 and the metal plate 306 is fixed to the primary gate 302). Subsequently, the collimator controller 120 controls the primary gate 302 and the secondary gate 301 to move together via the motor drive system 307, so as to align a center of the aperture between the primary gate 302 and the secondary gate 301 with the center of the opening 311.

During CT scan, a focal point of the X-ray tube 102 drifts due to a rise in temperature, so that the center of the aperture between the primary gate 302 and the secondary gate 301 and the center of the X-ray beam are not completely aligned. When the center of the aperture between the primary gate 302 and the secondary gate 301 and the center of the X-ray beam are not aligned, the collimator controller 302 moves both the primary gate 302 and the secondary gate 301 via the motor drive system 307 so as to track the focal point of the X-ray tube 102, as shown in FIG. 2D.

When width of the aperture between the primary gate 302 and the secondary gate 301 needs to be adjusted, the electromagnet 303-2 is released; the metal plate 306 is disengaged from the primary gate 302 ((being a secondary gate 301 when the electromagnet system 303 is disposed in the secondary gate 301 and the metal plate 306 is fixed to the primary gate 302) or the electromagnet system 303; and the secondary gate 301 returns to the original position under the action of the elastic member 305. Then, the collimator controller 120 controls the primary gate 302 to move along the Z direction under the action of the motor drive system 307, thereby selecting a desired aperture width. The electromagnet 303-2 of the electromagnet system 303 is trigged again, such that the primary gate 302 and the secondary gate 301 are closely engaged, and move together under the action of the motor drive system 307 to re-align the center of the aperture between the primary gate 302 and the secondary gate 301 with the center of the X-ray beam.

The collimator according to an embodiment of the present invention adopts an electromagnet system to engage or disengage the primary gate and the secondary gate, thereby simplifying the mechanical structure of the drive system for the primary gate and the secondary gate. By controlling the primary gate to move along the Z direction, continuously variable widths can be selected for the aperture between the primary gate and the secondary gate. By moving the primary gate and the secondary gate together, X-ray beam tracking and Z tracking can be achieved. Thus, in the collimator provided by the present invention, adjustment of the collimator aperture width, X-ray beam tracking and Z tracking can be concurrently realized only by way of a single-motor drive system.

In the CT collimator according to an embodiment of the present invention, the first gate and the second gate are engaged via a triggered electromagnet system. Therefore, continuous adjustment of the collimator aperture width and radiation beam tracking can be implemented by way of a single-motor drive system.

Although the present invention has been described with reference to specific embodiments, it shall be understood that the present invention is not limited to these specific embodiments. Skilled in the art will appreciate that various modifications, substitutions, changes and so on may be made to the present invention. For example, in the above embodiments one step or component may be divided into multiple steps or components; or, on the contrary, a plurality of steps or components in the above embodiments may be realized in one step or one component. All such variations should be within the scope of protection as long as they do not depart from the spirit of the present invention. In addition, the terms as used in the present specification and claims are not limitative, but descriptive. Moreover, according to actual needs, the entire or part of the features described in one specific embodiment can be incorporated into another embodiment.

What is claimed is:

1. A CT collimator, comprising:
a first gate and a second gate arranged in parallel on a slide rail, the first gate being fixed to a support rack of the CT collimator via elastic members;
an electromagnet system arranged on a side of one of the first gate and the second gate; and
a metal plate arranged on another side of the one of the first gate and the second gate relative to the electromagnet system, an end of the metal plate being fixed on the other of the first gate and the second gate and another end of the metal plate extending to be adjacent to the electromagnet system,
wherein the first gate and the second gate engage each other via the metal plate when the electromagnet system is triggered.

2. The CT collimator as claimed in claim 1, further comprising:
a single-motor drive system for driving the second gate to move on the slide rail via an actuator.

3. The CT collimator as claimed in claim 1, wherein the metal plate is a steel plate or non-metal magnetic material, and the metal plate has a length capable of extending to be adjacent to the electromagnet system when a maximum aperture is formed between the first gate and the second gate.

4. The CT collimator as claimed in claim 1, wherein the electromagnet system comprises an electromagnet and a support unit to support the electromagnet, the support unit fixing the electromagnet on the one of the first gate and the second gate, and the first gate and the second gate engage each other when the electromagnet is triggered.

5. The CT collimator as claimed in claim 1, wherein the electromagnet system comprises an electromagnet, a support unit to support the electromagnet, and an elastic member coupled to the electromagnet, wherein the metal plate is provided at an end of the electromagnet far away from the elastic member of the electromagnet system, the metal plate being housed in an opening provided on a support plate of the one of the first plate and the second plate, and wherein the electromagnet when triggered engages the first gate and the second gate via the metal plate provided on the electromagnet and the metal plate fixed on the other of the first gate and the second gate.

6. The CT collimator as claimed in claim 1, wherein the first gate comprises a first support plate and a first shielding material which is arranged proximate to a side of the second gate at the middle portion of the first support plate, and wherein the second gate comprises a second support plate and a second shielding material which is arranged proximate to a side of the first gate at the middle portion of the second support plate, the shielding materials blocking radiation beams which enter the CT collimator via an opening on a housing of the CT collimator.

7. The CT collimator as claimed in claim 6, wherein the shielding materials have a planar structure, and a width thereof is arranged to gradually decrease from a center of the shielding material to two ends thereof along relative edges of the shielding material.

8. The CT collimator as claimed in claim 6, wherein an aperture between the shielding materials has a rectangular shape, and the shielding materials have an arc structure whose center of circle is on a focal point of a radiation source outside the CT collimator.

9. The CT collimator as claimed in claim 6, wherein the elastic members comprises a stretchable and/or compressible spring.

10. The CT collimator as claimed in claim 9, wherein a length of the spring is arranged to enable a center of an aperture, formed between the shielding materials when the spring is not deformed, to deviate from the center of the opening so as to form a completely closed state.

11. The CT collimator as claimed in claim 9, wherein the spring is stretchable and compressible, and a length of the spring is arranged to enable the center of the aperture, formed between the shielding materials when the spring is not deformed, to directly face the center of the opening.

12. A radiograph CT system comprising:
   a CT collimator comprising:
      a first gate and a second gate arranged in parallel on a slide rail, the first gate being fixed to a support rack of the CT collimator via elastic members;
      an electromagnet system arranged on a side of one of the first gate and the second gate; and
      a metal plate arranged on another side of the one of the first gate and the second gate relative to the electromagnet system, an end of the metal plate being fixed on the other of the first gate and the second gate and another end of the metal plate extending to be adjacent to the electromagnet system,
      wherein the first gate and the second gate engage each other via the metal plate when the electromagnet system is triggered.

13. The radiograph CT system as claimed in claim 12, wherein the CT collimator further comprises:
   a single-motor drive system for driving the second gate to move on the slide rail via an actuator.

14. The radiograph CT system as claimed in claim 12, wherein the metal plate is a steel plate or non-metal magnetic material, and the metal plate has a length capable of extending to be adjacent to the electromagnet system when a maximum aperture is formed between the first gate and the second gate.

15. The radiograph CT system as claimed in claim 12, wherein the electromagnet system comprises an electromagnet and a support unit to support the electromagnet, the support unit fixing the electromagnet on the one of the first gate and the second gate, and the first gate and the second gate engage each other when the electromagnet is triggered.

16. The radiograph CT system as claimed in claim 12, wherein the electromagnet system comprises an electromagnet, a support unit to support the electromagnet, and an elastic member coupled to the electromagnet, wherein the metal plate is provided at an end of the electromagnet far away from the elastic member of the electromagnet system, the metal plate being housed in an opening provided on a support plate of the one of the first plate and the second plate, and wherein the electromagnet when triggered engages the first gate and the second gate via the metal plate provided on the electromagnet and the metal plate fixed on the other of the first gate and the second gate.

17. The radiograph CT system as claimed in claim 12, wherein the first gate comprises a first support plate and a first shielding material which is arranged proximate to a side of the second gate at the middle portion of the first support plate, and wherein the second gate comprises a second support plate and a second shielding material which is arranged proximate to a side of the first gate at the middle portion of the second support plate, the shielding materials blocking radiation beams which enter the CT collimator via an opening on a housing of the CT collimator.

18. The radiograph CT system as claimed in claim 17, wherein the shielding materials have a planar structure, and a width thereof is arranged to gradually decrease from a center of the shielding material to two ends thereof along relative edges of the shielding material.

19. The radiograph CT system as claimed in claim 17, wherein an aperture between the shielding materials has a rectangular shape, and the shielding materials have an arc structure whose center of circle is on a focal point of a radiation source outside the CT collimator.

20. The radiograph CT system as claimed in claim 12, wherein the radiograph CT system is an X-ray CT system.

* * * * *

UNITED STATES PATENT AND TRADEMARK OFFICE
CERTIFICATE OF CORRECTION

| | | |
|---|---|---|
| PATENT NO. | : 9,237,875 B2 | Page 1 of 1 |
| APPLICATION NO. | : 14/089877 | |
| DATED | : January 19, 2016 | |
| INVENTOR(S) | : Pan et al. | |

It is certified that error appears in the above-identified patent and that said Letters Patent is hereby corrected as shown below:

In the specification,

In Column 5, Line 8, delete "X-ray tube 104" and insert -- X-ray tube 102 --, therefor.

In Column 5, Line 10, delete "X-ray tube 104" and insert -- X-ray tube 102 --, therefor.

Signed and Sealed this
Twenty-third Day of August, 2016

Michelle K. Lee
*Director of the United States Patent and Trademark Office*